US009603835B2

(12) United States Patent
Vacher et al.

(10) Patent No.: US 9,603,835 B2
(45) Date of Patent: Mar. 28, 2017

(54) USE OF 3-(R)-[3-(2-METHOXYPHENYLTHIO)-2-(S)-METHYLPROPYL]AMINO-3,4-DIHYDRO-2H-1,5-BENZOXATHIEPINE FOR TREATING CANCER AND IN PARTICULAR FOR PREVENTING AND/OR TREATING CANCER METASTASES

(75) Inventors: Bernard Vacher, Castres (FR); Bruno Le Grand, Teyssode (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 268 days.

(21) Appl. No.: 14/342,011

(22) PCT Filed: Sep. 12, 2012

(86) PCT No.: PCT/EP2012/067780
§ 371 (c)(1),
(2), (4) Date: Mar. 24, 2014

(87) PCT Pub. No.: WO2013/037800
PCT Pub. Date: Mar. 21, 2013

(65) Prior Publication Data
US 2014/0206743 A1    Jul. 24, 2014

(30) Foreign Application Priority Data
Sep. 13, 2011   (FR) ..................... 11 58148

(51) Int. Cl.
*A61K 31/33*    (2006.01)
*A61K 31/39*    (2006.01)
*A61N 5/10*    (2006.01)
(52) U.S. Cl.
CPC ............... *A61K 31/39* (2013.01); *A61N 5/10* (2013.01)
(58) Field of Classification Search
CPC .................................................. C07D 401/12
USPC ...................................................... 514/183
See application file for complete search history.

(56) References Cited

U.S. PATENT DOCUMENTS

| 2004/0127552 A1 | 7/2004 | Vacher et al. |
| 2010/0221246 A1 | 9/2010 | Goydos et al. |

FOREIGN PATENT DOCUMENTS

| WO | WO 02/081464 A1 | 10/2002 |
| WO | WO 2012/049439 A1 | 4/2012 |

OTHER PUBLICATIONS

Anger et al., "Medicinal Chemistry of Neuronal Voltage-Gated Sodium Channel Blockers," Perspective, Journal of Medicinal Chemistry, vol. 44, No. 2, Jan. 18, 2001, pp. 115-137.
Arcangeli et al., "Targeting Ion Channels in Cancer: A Novel Frontier in Antineoplastic Therapy," Current Medicinal Chemistry, vol. 16, No. 1, 2009, pp. 66-93.
Biechele et al., "Chemical-Genetic Screen Identifies Riluzole as an Enhancer of Wnt/β-catenin signaling in Melanoma," Chemical Biology, vol. 17, No. 11, Nov. 24, 2010, pp. 1177-1182 (NIH Public Access Author Manuscript—pp. 1-11).
Bocquet et al., "F 15845, a new blocker of the persistent sodium current prevents consequences of hypoxia in rat femoral artery," XP-002673570, British Journal of Pharmacology, vol. 161, 2010, pp. 405-415.
Brackenbury et al., "The neonatal splice variant of Nav1.5 potentiates in vitro invasive behaviour of MDA-MB-231 human breast cancer cells," Breast Cancer Research and Treatment, vol. 101, 2007 (Published online Jul. 13, 2006), pp. 149-160.
Brisson et al., "Nav1.5 enhances breast cancer cell invasiveness by increasing NHE1-dependent H+ efflux in caveolae," Oncogene, vol. 30, 2011 (Published online Dec. 20, 2010), pp. 2070-2076.
Chioni et al., "A novel polyclonal antibody specifc for the Nav1.5 voltage-gated Na+ channel 'neonatal' splice form," Journal of Neuroscience Methods, vol. 147, 2005, pp. 88-98.
Fraser et al., "Voltage-Gated Sodium Channel Expression and Potentiation of Human Breast Cancer Metastasis," Clinical Cancer Research, vol. 11, No. 15, Aug. 1, 2005, pp. 5381-5389, including Correction thereto identified on p. 8224 dated Nov. 15, 2005.
Gao et al., "Expression of voltage-gated sodium channel α subunit in human ovarian cancer," Oncology Reports, vol. 23, 2010, pp. 1293-1299.
Gillet et al., "Beneficial effects of omega-3 long-chain fatty acids in breast cancer and cardiovascular diseases: voltage-gated sodium channels as a common feature?" Biochimie, vol. 93, 2011 (Available online Feb. 16, 2010), pp. 4-6.
Goldin, "Resurgence of Sodium Channel Research," Annual Review of Physiology, vol. 63, 2001, pp. 871-894.
House et al., "Voltage-Gated Na+ Channel SCN5A is a Key Regulator of a Gene Transcriptional Network That Controls Colon Cancer Invasion," Cancer Research, vol. 70, No. 17, Sep. 1, 2010 (Published online first Jul. 22, 2010), pp. 6957-6967.
International Search Report for International Application No. PCT/EP2012/067780, dated Nov. 23, 2012.
Le Grand et al., "Sodium Late Current Blockers in Ischemia Reperfusion: Is the Bullet Magic?" XP-002673569, Journal of Medicinal Chemistry, vol. 51, No. 13, 2008 (Published on Web Jun. 5, 2008), pp. 3856-3866.
Onkal et al., "Molecular pharmacology of voltage-gated sodium channel expression in metastatic disease: Clinical potential of neonatal Nav1.5 in breast cancer," XP-002673571, European Journal of Pharmacology, vol. 625, 2009 (Available online Oct. 14, 2009), pp. 206-219.

(Continued)

*Primary Examiner* — Raymond Henley, III
(74) *Attorney, Agent, or Firm* — Birch, Stewart, Kolasch & Birch, LLP

(57) ABSTRACT

The present invention relates to the use of 3-(R)-[3-(2-methoxyphenylthio)-2-(S)-methyl-propyl]amino-3,4-dihydro-2H-1,5-benzoxathiepine or one of the pharmaceutically acceptable salts thereof for treating cancer and particularly in preventing and/or treating cancerous metastases.

14 Claims, 1 Drawing Sheet

(56) References Cited

OTHER PUBLICATIONS

Roger et al., "Voltage-gated sodium channels potentiate the invasive capacities of human non-small-cell lung cancer cell lines," The International Journal of Biochemistry and Cell Biology, vol. 39, 2007 (Available online Jan. 20, 2007), pp. 774-786.

Wu et al., "The mechanism of the actions of oxaliplatin on ion currents and action potentials in differentiated NG108-15 neuronal cells," NeuroToxicology, vol. 30, 2009 (Available online May 5, 2009), pp. 677-685.

Manual of Medical Therapeutics, 27th Edition, Deparatment of Medicine, Washington School of Medicine, ed: M. Woodley et al., Chapter I.B., p. 490; Chapter I. p. 511, (1992) with English translation.

Tran et al., "Non-Anti-Mitotic Concentrations of Taxol Reduce Breast Cancer Cell Invasiveness", Biochemical and Biophysical Research Communications, vol. 379 (2009) pp. 304-308.

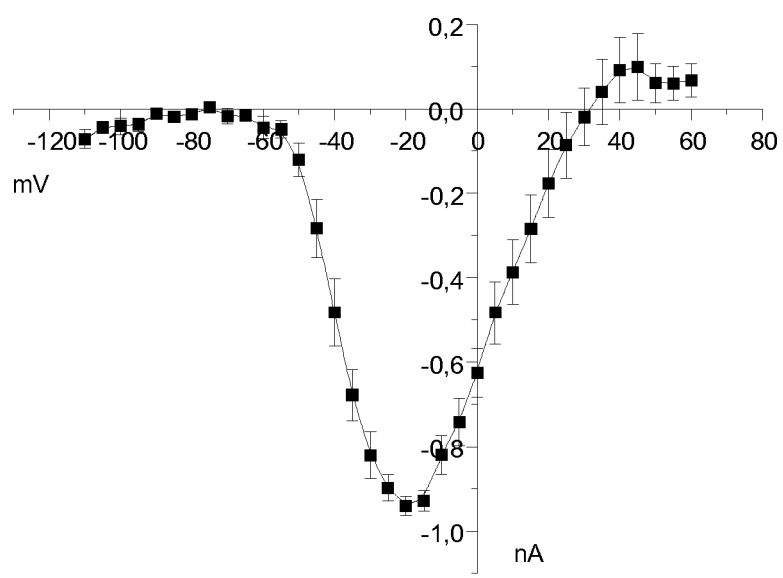

USE OF 3-(R)-[3-(2-METHOXYPHENYLTHIO)-2-(S)-METHYLPROPYL]AMINO-3,4-DIHYDRO-2H-1,5-BENZOXATHIEPINE FOR TREATING CANCER AND IN PARTICULAR FOR PREVENTING AND/OR TREATING CANCER METASTASES

The invention relates to the use of 3-(R)-[3-(2-methoxyphenylthio)-2-(S)-methyl-propyl]amino-3,4-dihydro-2H-1,5-benzoxathiepine or any of the pharmaceutically acceptable salts thereof in treating cancer and particularly in preventing and/or treating cancer metastases.

3-(R)-[3-(2-methoxyphenylthio)-2-(S)-methyl-propyl] amino-3,4-dihydro-2H-1,5-benzoxathiepine represented by the formula:

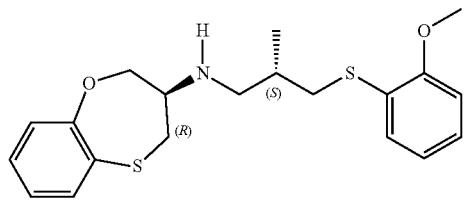

the pharmaceutically acceptable salts thereof and the use thereof in treating angina, heart failure, myocardial infarction and heart rhythm disorders are described in the patent application WO 02/081464.

Cancer can be defined broadly as a disease associated with the proliferation and uncontrolled dissemination of the body's cells that have become abnormal. It is one of the primary causes of mortality in developed countries and the number of new cases is constantly on the increase. However, due, among other things, to progress in anticancer treatments, the mortality rate due to cancer has decreased significantly. Anticancer treatments include, according to the type and degree of progression of the disease, surgery, radiotherapy and chemotherapy. In most cases, a combination of two or three approaches is required.

Radiotherapy is a locoregional treatment method for cancer, using ionising radiation to destroy cancer cells while sparing the neighbouring healthy tissue as much as possible. Chemotherapy consists of the use of substances liable to kill or limit the proliferation of cancer cells.

When cancer is detected at an early stage, i.e. before metastasis has occurred, the prognosis is relatively good. In practice, however, this only represents approximately 30% of cases. The tumour, known as the primary tumour, is then generally treated locally by means of surgery and/or radiotherapy; patients may receive additional chemotherapy intended to reduce the risks of recurrence and the onset of secondary tumours, or metastases.

Many types of cancer are capable of forming metastases which may be distant from the primary tumour and may arise several years after treating a primary tumour. This phenomenon can be explained by the existence of pre-angiogenic micrometastases or cells remaining without dividing for an extended period of time at the secondary site(s). In cancerology, the term metastases denotes secondary tumours forming due to the spreading of cells from a primary tumour, whether identified or not. The term micrometastases is used when the size of these secondary tumours does not exceed 2 mm.

Although the metastatic cells originate from the primary tumour, they are not exactly identical to the cells thereof. Indeed, these cells need to acquire a number of characteristics enabling the transition of the cells from the cancerous to the metastatic phenotype. However, the formation of metastases is a complex process, abbreviated herein as "metastatic process", whereby cancer cells leave the primary tumour and migrate to other parts of the body using the lymphatic and/or blood system. The metastatic process may be broken down into a plurality of steps: 1) the cancer cells separate from the primary tumour and bind with, simultaneously degrading, the proteins forming the extracellular matrix separating the tumour from the neighbouring tissue, 2) once there is a break in the matrix, they infiltrate the surrounding tissue including lymph and/or blood vessels, 3) they then survive in the circulation and are transported to the secondary site(s) where they emerge by extravasation, 4) they bind to a tissue and proliferate after activating the microenvironment and inducing angiogenesis to form a metastasis.

The term angiogenesis denotes the set of processes leading to the formation of new blood capillaries from the pre-existing vascular system.

In most cases of cancer, the mortality is not due to the primary tumour but to the metastases developing and multiplying on one or a plurality of organs.

The treatment of metastatic forms of cancer is essentially based on chemotherapy; radiotherapy and/or surgery are generally used additionally to relieve some symptoms. In practice, systemic chemotherapy treatments are however ineffective on metastases and have no effect on the metastatic process per se.

A further strategy has been developed which does not consist of destroying the metastases but rather preventing the growth thereof beyond a few mm by impeding tumour angiogenesis using substances inhibiting the proliferation of cells from the vascular endothelium.

The anti-angiogenic substances used in anticancer treatments include bevacizumab, sorafenib and sunitinib. Bevacizumab is a monoclonal antibody that binds with all the isoforms of vascular growth factor (VEGF) and prevents the binding thereof with VEGF receptors. Sorafenib and sunitinib are non-selective inhibitors of tyrosine kinase receptors, particularly those of VEGF. Anti-angiogenic substances have an indirect anti-metastatic activity since they enhance the delivery of the chemotherapeutic agents although they do not interfere with the metastatic process per se. Said medicinal products nonetheless involve serious drawbacks: 1) they reduce the density of tissue microvessels and interfere with normal repair processes; 2) they worsen coronary disease, cause arterial hypertension and thrombosis; 3) there are no predictive factors of the response or the onset of resistance, and 4) the cost thereof is very high.

Given the limitations of current treatments, there is a genuine medical need for substances capable of preventing metastases in patients suffering from cancer. Furthermore, it would appear to be very desirable for the substances in question to have direct anti-metastatic properties, thus complementary to those of existing medicinal products.

The ion channels have been described as being involved in the invasion and migration mechanisms necessary for the formation of metastases (Arcangeli et al. 2009, Curr. Med. Chem. 16, 66-93). The channels abnormally expressed in cancer cells include the Nav1.5 voltage-gated sodium channel (Onkal and Djamgoz 2009, Eur. J. Pharmacol. 625, 206-219). In the present invention, the term "Nav1.5" denotes the voltage-gated sodium channels wherein the alpha subunit forming the channel pore is coded by the SNC5A gene (also known as H1) situated on chromosome 3. The alpha subunit may be associated with one or a plurality of auxiliary subunits (referred to as beta subunit(s)) coded by the SNC1B, SNC2B, SNC3B, SNC4B genes located on chromosomes 11 and 19.

In this way, it has been demonstrated that the expression of functional Nav1.5 channels in ovarian cancer cells significantly increases the metastatic potential thereof (Gao et al. 2010, Oncology Reports 23, 1293-1299). Similarly, functional Nav1.5 channels have been detected in highly metastatic breast cancer (Brisson et al. 2011, Oncogene 30, 2070-2076) or colon cancer biopsies (House et al. 2010, Cancer Res. 70, 6957-6967) whereas they are not found in healthy cells from the corresponding tissue or those of tumours with little or no metastasis. Nav1.5 channels have also been detected in a plurality of lung cancer biopsies and tumour lines (Roger et al. 2007, Int. J. Biochem. Cell Biol. 39, 774-786). Nav1.5 type channel expression or overexpression has further been proposed as a diagnostic tool in respect of the metastatic potential of cancer cells (Fraser et al. 2005, Clin. Cancer Res. 11, 5381-5389). It has also been suggested that the beneficial effect of long-chain unsaturated fatty acids in breast, colon and prostate cancers could be associated with the inhibitory properties thereof of in respect of the Nav1.5 sodium current, although the mechanism of action thereof is not known (Gillet et al. 2011, Biochimie 93, 4-6). In vitro experiments indicate that Nav1.5 channel blockers such as tetrodotoxin or polyclonal antibodies targeted against the neonatal form of the Nav1.5 channel attenuate the metastatic potential in a plurality of cancer cell lines (Chioni et al. 2005, J. Neurosci. Methods 147, 88-98).

A range of data thus indicates that the sodium current produced by the Nav1.5 channel plays a major role in the metastatic process of cancer cells, at least in some types of cancer, particularly breast, lung, prostate, colon, bladder, ovarian, testicular, skin, thyroid or stomach cancer. The mechanisms whereby Nav1.5 channels potentiate metastasis formation have not been elucidated but a number of hypotheses have been suggested such as, for example, adhesion modification, proteolytic enzyme regulation. In conclusion, the Nav1.5 channel thus emerges as a potential target for preventing metastasis formation.

Given the ubiquitous role of the Nav1.5 channel, the use thereof as a therapeutic target for developing an anticancer and/or anti-metastatic agent is nonetheless complex. Indeed, the Nav1.5 channel is widely distributed in the body notably in cardiac and vascular cells (Goldin 2001, Annu. Rev. Physiol. 63, 871-894).

In cardiomyocytes, opening the Nav1.5 channel triggers an incoming sodium current that can be deactivated according to at least two modes, each characterised by the channel closure kinetics: rapid inactivation and slow inactivation. Rapid inactivation induces the so-called "rapid" Nav1.5 current only lasting a few milliseconds, whereas slow inactivation generates the so-called "slow" current lasting several tens of milliseconds. The rapid Nav1.5 current plays a fundamental role in normal heart function where it activates and propagates cardiac action potential. On the other hand, that of the slow current does not seem to be important in normal cardiac function and is only produced or significantly amplified in cardiac and vascular cells subjected to stress (Bocquet et al. 2010, Br. J. Pharmacol. 161, 405-415).

Surprisingly, the inventors demonstrated that 3-(R)-[3-(2-methoxyphenylthio)-2-(S)-methyl-propyl]amino-3,4-dihydro-2H-1,5-benzoxathiepine which is a selective slow Nav1.5 current inhibitor, also inhibits the sodium current produced by the Nav1.5 sodium channels found in cancer cells, abbreviated herein as "metastatic Nav1.5 current".

Based on this observation, it has emerged that the metastatic Nav1.5 current and the slow Nav1.5 current have sufficiently similar biophysical characteristics to both be recognised by 3-(R)-[3-(2-methoxyphenylthio)-2-(S)-methyl-propyl]amino-3,4-dihydro-2H-1,5-benzoxathiepine.

It has also emerged that the metastatic Nav1.5 current and the rapid cardiac Nav1.5 current are actually dissociable. Indeed, the inventors have demonstrated that 3-(R)-[3-(2-methoxyphenylthio)-2-(S)-methyl-propyl]amino-3,4-dihydro-2H-1,5-benzoxathiepine does not affect normal cardiovascular system function under the control of the rapid Nav1.5 current, even at high doses. 3-(R)-[3-(2-methoxyphenylthio)-2-(S)-methyl-propyl]amino-3,4-dihydro-2H-1,5-benzoxathiepine thus has the selectivity of action required for the use thereof as an anti-metastatic agent since it blocks the metastatic Nav1.5 current without interfering with the rapid Nav1.5 current essential for normal cardiac and vessel function.

The Nav1.5 channel inhibitors/blockers include numerous non-Nav1.5 selective compounds such as natural toxins, therapeutic molecules (e.g. anaesthetic, antiarrhythmic agents) and insecticides (Anger et al. 2001, J. Med. Chem. 44, 115-137). Only two medicinal products are described as preferential slow cardiac Nav1.5 current blockers: ranolazine (RN 95635-55-5) and riluzole (RN 1744-22-5), but they are relatively ineffective and non-selective with respect to said current. Furthermore, they interact with other molecular targets than the Nav1.5 channel. Interestingly, riluzole has been reported as having an anti-metastatic activity in melanomas, however, this activity involves other mechanisms than slow Nav1.5 sodium current inhibition (US 20100221246; Biechele et al. 2010, Chemistry & Biology 17, 1177-1182; Wu et al. 2009, NeuroToxicology 30, 677-685).

The present invention thus provides a novel means for fighting cancer and more particularly for preventing or treating metastases thereof, via direct action on the metastatic process, which no existing agent is capable of performing.

BRIEF DESCRIPTION OF THE DRAWINGS

FIG. 1 shows the measurement of the Voltage-dependent current $I_{Na}$.

Although the Nav1.5 channel has been identified in various types of metastatic cancer such as breast, lung, prostate, or colon cancer, it is obvious that the use of 3-(R)-[3-(2-methoxyphenylthio)-2-(S)-methyl-propyl]amino-3,4-dihydro-2H-1,5-benzoxathiepine is not limited to said forms of cancer but applies to all forms of cancer wherein the cells express, inter alia, the Nav1.5 channel.

More specifically and by way of example, it is demonstrated according to the invention that 3-(R)-[3-(2-methoxyphenylthio)-2-(S)-methyl-propyl]amino-3,4-dihydro-2H-1,5-benzoxathiepine or one of the pharmaceutically acceptable salts thereof blocks the metastatic Nav1.5 current in a highly metastatic human mammary cancer tumour line. Given the relationship established between the current produced by the Nav1.5 channels found in cancer cells and the tendency thereof to form metastases, detecting inhibitory properties of said current is thus equivalent to detecting anti-metastatic properties. Furthermore, the inventors demonstrated that 3-(R)-[3-(2-methoxyphenylthio)-2-(S)-methyl-propyl]amino-3,4-dihydro-2H-1,5-benzoxathiepine was not cytotoxic.

The present invention relates to 3-(R)-[3-(2-methoxyphenylthio)-2-(S)-methyl-propyl]amino-3,4-dihydro-2H-1,5-benzoxathiepine or one of the pharmaceutically acceptable salts thereof for use as a medicinal product intended for treating cancer and more particularly for preventing or treating metastases thereof.

In the present invention, the term "pharmaceutically acceptable" refers to molecular entities and compositions not producing any adverse or allergic effect or any other undesirable reaction when administered to a human. When used herein, the term "pharmaceutically acceptable excipient" includes any diluent, adjuvant or excipient, such as preservative agents, filling agents, disintegrating, wetting, emulsifying, dispersing, antibacterial or antifungal agents, or else agents suitable for delaying intestinal and digestive absorption and resorption. The use of these media or vectors is well-known to those skilled in the art.

The term "pharmaceutically acceptable salts" of a compound denotes salts which are pharmaceutically acceptable, as defined herein and having the sought pharmacological activity of the parent compound. Such salts comprise: acid addition salts formed with mineral acids such as hydrochloric acid, hydrobromic acid, sulphuric acid, nitric acid, phosphoric acid and similar or formed with organic acids such as acetic acid, benzenesulphonic acid, benzoic acid, camphorsulphonic, citric acid, ethane-sulphonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartaric acid, tartaric acid, p-toluenesulphonic acid, trimethylacetic acid, trifluoroacetic acid and similar.

The pharmaceutically acceptable salts also include the solvent addition forms (solvates) or crystalline (polymorphous) forms as defined herein, of the same acid addition salt.

The invention also relates to the use of 3-(R)-[3-(2-methoxyphenylthio)-2-(S)-methyl-propyl]amino-3,4-dihydro-2H-1,5-benzoxathiepine or one of the pharmaceutically acceptable salts thereof, in patients presenting one or more cancerous tumours wherein the cells express, inter alia, the Nav1.5 voltage-gated sodium channel.

The present invention further relates to a pharmaceutical composition containing, as an active agent, 3-(R)-[3-(2-methoxyphenylthio)-2-(S)-methyl-propyl]amino-3,4-dihydro-2H-1,5-benzoxathiepine or one of the pharmaceutically acceptable salts thereof and at least one pharmaceutically acceptable excipient, for the use thereof in treating cancer and more particularly for preventing or treating cancer metastases. Preferentially, the cancers concerned by the composition according to the present invention are: breast, lung, prostate, colon, bladder, ovarian, testicular, skin, thyroid or stomach cancer.

Preferably, the pharmaceutical composition according to the invention is intended for patients in whom tumour cells express, inter alia, the Nav1.5 channel. The presence of said channel in the patient's tumour cells may be detected by the presence of the messenger RNA of the SCN5A gene and/or of the channel protein per se. The messenger RNA and/or the protein may be detected by means of techniques well-known to those skilled in the art such as, for example, PCR (polymerase chain reaction), Western blot or in situ hybridisation. The cells may be obtained from samples taken from the primary tumour, metastases, lymph nodes or blood and be analysed directly or cultured in vitro before being analysed.

The pharmaceutical composition according to the invention may be administered with one or more further active agents, such as an anticancer agent, or in association with a radiotherapy or surgical treatment, or with a combination thereof. The administration may then be simultaneous, separate or staggered in relation to the other treatment(s). It may also be used for the entire duration or for a shorter or longer period than that of the other anticancer treatment.

The pharmaceutical compositions according to the present invention are formulated for administration to humans. The compositions according to the invention may be administered by the oral, sublingual, subcutaneous, intramuscular, intravenous, transdermal, local or rectal or also intra-nasal route. In this case, the active ingredient may be administered in unitary dosage forms, mixed with conventional pharmaceutical carriers, to humans. Suitable unitary dosage forms include oral forms such as tablets, capsules, powders, granules and oral solutions or suspensions, sublingual and buccal dosage forms, subcutaneous or transdermal, topical, intramuscular, intravenous, intra-nasal or intraocular dosage forms, rectal dosage forms.

When a solid composition in tablet form is prepared, the main active ingredient is mixed with a pharmaceutical vehicle such as gelatine, starch, lactose, magnesium stearate, talc, gum arabic, silica or equivalents. The tablets may be coated with sucrose or other suitable materials or may be treated so as to have a sustained or delayed activity and continuously release a predefined quantity of active ingredient.

A capsule preparation is obtained by mixing the active ingredient with a diluent and pouring the mixture obtained into soft or hard capsules.

A preparation in syrup or elixir form may contain the active ingredient in conjunction with a sweetener, an antiseptic, along with an agent providing flavour and a suitable colorant.

Water-dispersible powders or granules may contain the active ingredient mixed with dispersion agents or wetting agents, or suspension agents, along with flavouring substances or sweeteners.

For rectal administration, suppositories are used, which are prepared with binders melting at rectal temperature, for example cocoa butter or polyethylene glycols.

For parenteral (intravenous, intramuscular, intradermal, subcutaneous), intra-nasal or intraocular administration, aqueous suspensions, isotonic saline solutions or sterile and injectable solutions containing pharmacologically compatible dispersion agents and/or wetting agents are used.

The active ingredient may also be formulated in microcapsule form, optionally with one or a plurality of additive carriers.

Advantageously, the pharmaceutical composition according to the present invention is intended for oral or intravenous administration.

The pharmaceutical composition according to the present invention may comprise further active ingredients resulting in an additional or optionally synergistic effect.

The dosages of 3-(R)-[3-(2-methoxyphenylthio)-2-(S)-methyl-propyl]amino-3,4-dihydro-2H-1,5-benzoxathiepine or one of the pharmaceutically acceptable salts thereof in the compositions according to the invention may be adjusted to obtain a quantity of substance which is effective for obtaining the therapeutic response sought for a particular composition with the administration method. The effective dose of the compound according to the invention varies according to numerous parameters such as, for example, the selected administration route, the weight, age, gender and sensitivity of the subject to be treated. Consequently, the optimal dosage should be determined by the relevant specialist according to the parameters deemed relevant. Although the effective doses can vary in large proportions, the daily doses could range between 1 mg and 1000 mg per 24 hours, and preferentially between 1 and 200 mg, for an adult with an average weight of 70 kg, in one or more doses.

The following example enables a clearer understanding of the invention without limiting the scope thereof.

Merely as an illustration, the inventors chose to use the MDA-MB-231 line, which is a highly metastatic human mammary adenocarcinoma line, in the experiment. Indeed, it has been demonstrated that said cells express, inter alia, functional Nav1.5 voltage-gated sodium channels and that blocking said channel using various pharmacological tools reduced the metastatic potential thereof (Brackenbury et al. 2007, Breast Cancer Res. Treat. 101, 149-160). However, the pharmacological tools in question are not suitable for precise characterisation of the nature of the Nav1.5 sodium current involved in the metastatic process. However, the inventors demonstrated by means of patch-clamp experiments in a "whole cell" configuration, conducted on MDA-MB-231 cells, that 3-(R)-[3-(2-methoxyphenylthio)-2-(S)-methyl-propyl]amino-3,4-dihydro-2H-1,5-benzoxathiepine reduced the metastatic Nav1.5 current in a concentration-dependent fashion ($IC_{50}$=1.5 μM). For this reason, the inventors consider that 3-(R)-[3-(2-methoxyphenylthio)-2-(S)-methyl-propyl]amino-3,4-dihydro-2H-1,5-benzoxathiepine has anti-metastatic properties in relation to cancer cells expressing the Nav1.5 channel. As such, it is important to note that numerous types of metastatic cancer have been reported as expressing the Nav1.5 channel.

Method

Cell culture: the MDA-MB-231 cells are cultured in a Dulbecco's modified Eagle's medium, (Life Technologies LTD, Paisley, UK) supplemented with 4 mM L-glutamine and 10% foetal calf serum. The cells are inoculated in 100 mm culture dishes and placed in an incubator at 37° C., 100% moisture and 5% $CO_2$.

Electrophysiological measurements in "whole cell" configuration: the patch pipette (resistance 5-15 MΩ) contains a solution of: 5 mM NaCl, 145 mM CsCl, 2 mM $MgCl_2$, 1 mM $CaCl_2$, 10 mM HEPES and 11 mM EGTA, the pH is adjusted to 7.4 with CsOH. The reference electrode is immersed in the extracellular medium consisting of a solution of: 140 mM NaCl, 4 mM KCl, 2 mM $MgCl_2$, 11 mM glucose, 10 mM HEPES, the pH is adjusted to 7.4 with NaOH. These two electrodes are connected to an Axopatch 200B amplifier (Axon Instrument). The currents are filtered using a Bessel filter at a frequency of 5 kHz and are sampled at a frequency of 5 kHz using the Digidata interface (1200). The data acquisition and analysis are performed using pClamp software (Axon Instrument). The holding potential is set to −110 mV to record the maximum Nav channel activity.

Two protocols were used:
1/ "Voltage-dependent current $I_{Na}$" protocol for observing the maximum amplitude of $I_{Na}$ according to the voltage applied. Depolarisations in 5 mV stages are performed at a frequency of 0.2 Hz, from −110 to +60 mV. The depolarisation interval lasts 600 ms (see FIG. 1).
2/ "Repeated depolarisation" protocol for measuring the effect of the test product on the current amplitude. For this, depolarisations at −20 mV are performed in sequence at a frequency of 0.5 Hz. The depolarisation interval lasts 25 ms.

Results

The cells tested express a maximum amplitude current in the order of 900 pA. The current activation threshold is situated at −50 mV, the current peak around −20 mV and the reversal potential at +30 mV (FIG. 1). The current is cancelled in the absence of $Na^+$ ions in the medium, confirming that the current in question is a sodium current. The peak current inhibition with tetrodotoxin (Sigma) is merely partial: 30±7% at 1 μM and 54±8% at 5 μM, indicating that the current in question is tetrodotoxin-resistant.

Moreover, the inventors demonstrated in vivo that 3-(R)-[3-(2-methoxyphenylthio)-2-(S)-methyl-propyl]amino-3,4-dihydro-2H-1,5-benzoxathiepine does not interfere with normal cardiac function even at high doses.

The present invention is thus characterised: 1) in that 3-(R)-[3-(2-methoxyphenylthio)-2-(S)-methyl-propyl]amino-3,4-dihydro-2H-1,5-benzoxathiepine has a direct action on the metastatic process and, as such, is complementary to existing treatments; 2) in that 3-(R)-[3-(2-methoxyphenylthio)-2-(S)-methyl-propyl]amino-3,4-dihydro-2H-1,5-benzoxathiepine has a selective action on cancer cells without interfering, at anti-metastatic doses, with the other functions in which the Nav1.5 sodium channels are involved such as normal cardiac and vascular function.

The invention claimed is:

1. A method for treating cancer comprising the administration to a patient in need thereof of an effective amount of 3-(R)-[3-(2-methoxyphenylthio)-2-(S)-methyl-propyl]amino-3,4-dihydro-2H-1,5-benzoxathiepine or one of the pharmaceutically acceptable salts thereof; wherein the patient suffers from breast, lung, prostate, colon, bladder, ovarian, testicular, skin, thyroid or stomach cancer.

2. The method according to claim 1, for preventing or treating cancer metastases.

3. The method according to claim 1, wherein the patient presents one or more cancerous tumours, the cells of which express, inter alia, the Nav1.5 voltage-gated sodium channel.

4. A method for treating cancer comprising the administration to a patient in need thereof of an effective amount of a pharmaceutical composition containing, as an active agent, 3-(R)-[3-(2-methoxyphenylthio)-2-(S)-methyl-propyl]amino-3,4-dihydro-2H-1,5-benzoxathiepine or one of the pharmaceutically acceptable salts thereof and at least one pharmaceutically acceptable excipient; wherein the patient suffers from breast, lung, prostate, colon, bladder, ovarian, testicular, skin, thyroid or stomach cancer.

5. The method according to claim 4, for preventing or treating cancer metastases.

6. The method according to claim 4, wherein the patient presents one or more cancerous tumours, the cells of which express, inter alia, the Nav1.5 voltage-gated sodium channel.

7. The method according to claim 4, wherein the patient undergoes chemotherapy treatment.

8. The method according to claim 7, for the simultaneous, separate or staggered use of the pharmaceutical composition in relation to the chemotherapy treatment.

9. The method according to claim 4, wherein the patient undergoes radiotherapy and/or surgical treatment(s).

10. The method according to claim 9, for the simultaneous, separate or staggered use thereof in relation to the other radiotherapy and/or surgical treatment(s).

11. The method according to claim 4, wherein the patient undergoes chemotherapy treatment and radiotherapy and/or surgical treatment(s).

12. The method according to claim 11, for the simultaneous, separate or staggered use thereof in relation to the other chemotherapy treatment and radiotherapy and/or surgical treatment(s).

13. The method according to claim 4, wherein the pharmaceutical composition is administered orally or intravenously.

14. The method according to claim 4, wherein the pharmaceutical composition is in the form of a daily dosage unit of 3-(R)-[3-(2-methoxyphenylthio)-2-(S)-methyl-propyl] amino-3,4-dihydro-2H-1,5-benzoxathiepine or one of the pharmaceutically acceptable salts thereof between 1 and 1000 mg.

* * * * *